US010314251B2

(12) United States Patent
Gagne et al.

(10) Patent No.: US 10,314,251 B2
(45) Date of Patent: Jun. 11, 2019

(54) SYSTEM, APPARATUS AND METHOD FOR GROWING MARIJUANA

(71) Applicant: AVID GROWING SYSTEMS INC., St. Catharines (CA)

(72) Inventors: Patrick Gagne, Niagara Falls (CA); Jody Clugston, Stevensville (CA); Jonathon Pounder, Thorold (CA)

(73) Assignee: Avid Growing Systems Inc., St. Catharines, Ontario (CA)

( * ) Notice: Subject to any disclaimer, the term of this patent is extended or adjusted under 35 U.S.C. 154(b) by 0 days.

(21) Appl. No.: 15/493,710

(22) Filed: Apr. 21, 2017

(65) Prior Publication Data

US 2017/0223912 A1 Aug. 10, 2017

Related U.S. Application Data

(63) Continuation of application No. PCT/CA2015/051054, filed on Oct. 20, 2015.
(Continued)

(51) Int. Cl.
*A01G 31/02* (2006.01)
*G01N 29/06* (2006.01)
(Continued)

(52) U.S. Cl.
CPC ............. *A01G 31/02* (2013.01); *A01G 9/246* (2013.01); *A01G 9/247* (2013.01); *A01G 25/16* (2013.01);
(Continued)

(58) Field of Classification Search
CPC ...... A01G 31/00; A01G 31/02; A01G 31/001; A01G 31/006; A01G 2031/006
(Continued)

(56) References Cited

U.S. PATENT DOCUMENTS 6,219,966 B1 * 4/2001 Lapointe ................ A01G 31/02
47/62 C
6,276,089 B1 * 8/2001 Boisclair ................ A01G 31/02
47/60
(Continued)

FOREIGN PATENT DOCUMENTS

CA 1308909 10/1992
CA 2518789 A1 3/2006
(Continued)

OTHER PUBLICATIONS

Translation of Abstract for NL1031466.*
(Continued)

*Primary Examiner* — Monica L Williams
*Assistant Examiner* — Aaron M Rodziwicz
(74) *Attorney, Agent, or Firm* — Haukaas Fortius PLLC; Michael H. Haukaas

(57) ABSTRACT

Systems, apparatuses and methods for growing marijuana plants, particularly for regulated purposes, for example medical purposes or in some jurisdictions recreational purposes, have automated subsystems with sensors to provide feedback information about system, apparatus and plant growth parameters to one or more controllers so that the one or more controllers can alter one or more parameters to provide optimal conditions for the growing and harvesting of the marijuana plants. In particular aspects, the systems, apparatuses and methods provide for control of odors produced during the growing of marijuana, root management of the marijuana plants and control over important levels of chemicals provided to the plants, for example enzymes and flavor additives.

7 Claims, 5 Drawing Sheets

Related U.S. Application Data

(60) Provisional application No. 62/066,568, filed on Oct. 21, 2014.

(51) Int. Cl.
*G01N 29/27* (2006.01)
*A01G 9/24* (2006.01)
*A01G 25/16* (2006.01)
*A01G 31/00* (2018.01)

(52) U.S. Cl.
CPC ......... *G01N 29/0654* (2013.01); *G01N 29/27* (2013.01); *A01G 2031/006* (2013.01); *G01N 2291/015* (2013.01); *G01N 2291/0427* (2013.01); *G01N 2291/106* (2013.01); *G01N 2291/2695* (2013.01); *G01N 2291/2698* (2013.01); *Y02A 40/268* (2018.01); *Y02A 40/272* (2018.01); *Y02P 60/216* (2015.11)

(58) Field of Classification Search
USPC .............................................. 47/60
See application file for complete search history.

(56) References Cited

U.S. PATENT DOCUMENTS

| | | | |
|---|---|---|---|
| 6,660,310 B2 | 12/2003 | Carlson | |
| 8,448,379 B2* | 5/2013 | Igarashi | A01G 31/06 47/62 R |
| 8,726,568 B2* | 5/2014 | Wilson | A01G 31/00 47/62 R |
| 9,345,207 B2* | 5/2016 | Juncal | A01G 31/02 |
| 9,807,949 B2* | 11/2017 | Hamlin | A01G 31/02 |
| 2002/0184820 A1 | 12/2002 | Mauney | |
| 2012/0060416 A1 | 3/2012 | Brusatore | |
| 2014/0208642 A1 | 7/2014 | Henman et al. | |
| 2014/0260131 A1 | 9/2014 | Burkhauser | |
| 2016/0143228 A1* | 5/2016 | De Groot | A01G 9/24 700/284 |

FOREIGN PATENT DOCUMENTS

| | | | |
|---|---|---|---|
| CA | 2873166 A1 * | 11/2012 | ............. A01G 31/02 |
| CA | 2873166 A1 | 11/2012 | |
| CA | 2876425 A1 | 1/2014 | |
| NL | 1031466 C2 * | 10/2007 | ............. A01G 7/045 |
| WO | 2014102553 A1 | 7/2014 | |

OTHER PUBLICATIONS

"1st Marijuana Growers Page," accessed on the internet at http://www.1stmarijuanagrowerspage.com/how-to-grow-marijuana-3.html/, retrieved Sep. 22, 2014, 15pgs.

"A Basic Design Guide for Clean Room Applications," PDH Online/PDH Center, 2012, 62pgs.

"Is "100% Smell Proof" Even Attainable," accessed on the internet at http://forum.grasscity.com/indoor-medical-maroijuana-growing/1302270-100-smell-proof-e . . . , retrieved Sep. 22, 2014, 5pgs.

"Superflower 3.0 Grow Box Review," accessed on the internet at http://howtogrowmarijuama.com/superflower-grow-box, retrieved Sep. 22, 2014, 7pgs.

"The Best Stealth Grow Box for the Money," accessed on the Internet at http://collegeofcannabis.com/reviews/the-best-stealth-grow-box-for-the-money/, retrieved Sep. 22, 2014, 5pgs.

Danko, D., "Cannabis Cultivation Basics," High Times, Dec. 26, 2013, accessed on the Internet at http://www.hightimes.com/read/cannabis-cultivation-basics, retrieved Apr. 20, 2017, 8pgs.

International Search Report and Written Opinion of the ISA/CA dated Jan. 25, 2016 in Int'l Application No. PCT/CA2015/051054; 14pgs.

\* cited by examiner

SYSTEM, APPARATUS AND METHOD FOR GROWING MARIJUANA

CROSS-REFERENCE TO RELATED APPLICATIONS

This application is a continuation under 35 U.S.C. 111(a) of International Application No. PCT/CA2015/051054 filed Oct. 20, 2015 and published as WO 2016/061672 on Apr. 28, 2016, which claims the benefit of U.S. Provisional Application No. 62/066,568 filed Oct. 21, 2014, the entire contents of each of which are herein incorporated by reference.

FIELD

This application relates to horticulture, in particular to the growing of marijuana under controlled conditions.

BACKGROUND

Medical marijuana (marihuana) production in Canada must comply with the Health Canada imposed regulations, which are among the strictest in the world. Wth respect to the plants themselves little guidance is given to any specific growth method, but certain conditions are imposed. Growing areas may not give off odors or emit pollen. And, final product must be capable of passing strict lab testing for both inorganics such as pesticides or heavy metals which may not be present, and also organics such as mold spores, mildew, bacteria etc., which also may not be present.

Given these requirements certain growing conditions are thus dictated. The plants must be protected from exposure to any of the above sources of contamination in their air or water. They may not be treated with any pesticides that might end up in the final product which are not permitted there. The growing conditions should prevent the formation of any mold or mildew even if there is growth potential. Odors and pollen must be controlled. Human factors of contamination must be eliminated as much as possible.

From a commercial standpoint other conditions are dictated. Whatever facility is used to grow the plants, the growing area is preferably compact and space efficient, resource frugal, designed to minimize human resources, designed to minimize and isolate crop loss, designed to minimize growth time of a crop, adaptable to existing buildings and structures, designed to allow for product customization for market differentiation, designed to minimize the knowledge needed to successfully operate the system and designed to allow for easy consultation with experts if there is a problem.

In light of the above conditions, a system for managing plant growth which meets all the regulatory requirements and produces optimized yields of customized products at an accelerated growth rate compared to other methods of production while using less resources is desirable. Such systems would ideally be fully automated to minimize human contact with the plants, to allow the system to operate with minimal human resources, and to notify an operator when attention is required rather than having to be watched constantly.

SUMMARY

In one aspect, there is provided an apparatus for growing marijuana plants comprising: a growth chamber containing a climate controlled micro-climate under negative air pressure; at least one marijuana plant support structure situated in the growth chamber, the plant support structure configured to support a marijuana plant whereby roots of the marijuana plant are exposed to air in the growth chamber; a water management system in fluid communication with the plant support structure configured to deliver water and other chemical components to at least the roots of the marijuana plant; at least one sensor configured to sense at least one parameter of the growth chamber, water management system or marijuana plant; and, a controller in electronic communication with the at least one sensor and one or more of the growth chamber and water management system, the controller configured to control the growth chamber, water management system or both in response to a signal from the at least one sensor.

In one aspect, there is provided a method of growing marijuana plants comprising: providing at least one marijuana plant in a growth chamber containing a climate controlled micro-climate under negative air pressure whereby roots of the marijuana plant are exposed to air in the growth chamber; automatically delivering water and other chemical components to at least the roots of the marijuana plant; automatically determining at least one parameter of the growth chamber, water, other chemical components or marijuana plant; and, automatically controlling the growth chamber, water, other chemical components or any combination thereof in response to the determining of the at least one parameter.

In one aspect, there is provided a marijuana plant produced by growing marijuana plants by a method as defined above.

In one aspect, there is provided a vendible portion of a marijuana plant comprising levels of a flavoring elevated beyond naturally occurring levels of the flavoring.

In one aspect, there is provided a system comprising: a plurality of automated apparatuses for growing marijuana plants, each automated apparatus comprising a dedicated controller, a dedicated heating-ventilation-and-cooling (HVAC) component and one or more sensors for sensing one or more growth parameters; a central controller in electronic communication with the one or more sensors of each automated apparatus, the central controller configured to supervise the dedicated controllers and implement set points for the one or more growth parameters at different stages of growth of the marijuana plants in response to signals received from the one or more sensors of each automated apparatus.

In one aspect, there is provided a facility for growing marijuana plants, comprising: an apparatus for growing marijuana plants, the apparatus comprising a sensor for detecting odors escaping from the apparatus; and, a building comprising a climate controlled interior space under positive air pressure from air flowing into the interior space after being purified by at least one air filter, the apparatus for growing marijuana plants situated in the interior space, the building further comprising a controller for controlling climate in the interior space, the sensor for detecting odors in electronic communication with the controller, and the controller configured to change the air pressure in the inner space from positive to negative when the sensor detects odors escaping from the apparatus.

The facilities, systems, apparatuses and methods for growing marijuana plants are especially suited for growing marijuana for regulated purposes, for example recreational and medical purposes. The facilities, systems, apparatuses and methods have automated subsystems with sensors to provide feedback information about one or more parameters to one or more controllers so that the one or more controllers can alter one or more of parameters to provide optimal conditions for the growing and harvesting of the marijuana plants while respecting regulatory and environmental concerns. In particular aspects, the facilities, systems, apparatuses and methods provide for control of odors produced during the growing of marijuana, root management of the marijuana plants and control over important levels of chemicals provided to the plants, for example enzymes and flavor additives.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

BRIEF DESCRIPTION OF THE DRAWINGS

For clearer understanding, preferred embodiments will now be described in detail by way of example, with reference to the accompanying drawings, in which.

DETAILED DESCRIPTION

Figure 1:
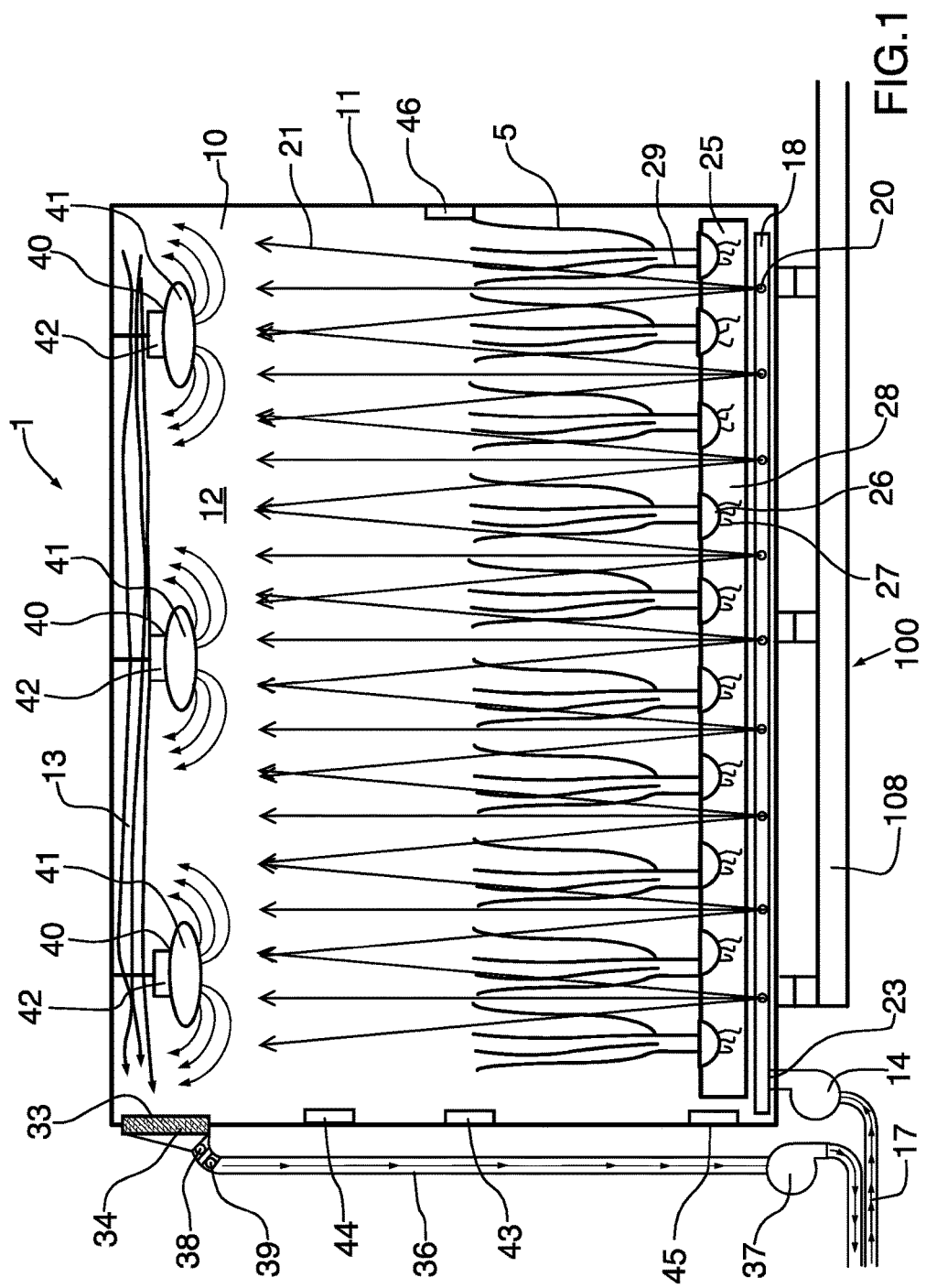
FIG. 1 depicts a schematic side view of an embodiment of an apparatus for growing marijuana plants comprising a growth chamber.

Methods, apparatuses, systems and facilities for growing marijuana plants involve various logical and physical subsystems that interact in feedback loops to provide the desired growing conditions while controlling exposure of the plants to sources of contamination (e.g. pesticides, mold, mildew) in the air or water and while controlling odors and pollen produced by the growing marijuana plants. Human interaction with the subsystems may be minimized by automated control with feedback signals from various sensors in the system. Problem detection may be mitigated by automatic adjustment of operational parameters and alerts provided to an operator permitting the operator to intervene manually where required. The following is a description of various logical and physical subsystems that may be present in marijuana plant growing methods, apparatuses, systems and facilities of the present invention.

Micro-climate Environment Subsystem

The micro-climate for growing marijuana plants is contained within a physical structure, i.e. the growth chamber. The growth chamber comprises structures configured for planting and irrigating marijuana plants, providing air flow through the growth chamber and past the plants in the growth chamber, illuminating the plants and controlling conditions of temperature, pressure and/or humidity in the growth chamber.

The structure for planting the marijuana plants may comprise an aeroponic structure that permits exposure of roots of the plant to air in the micro-climate while permitting an irrigation solution to be sprayed on the roots. In one embodiment, the planting structure comprises tubes, preferably oriented horizontally in the growth chamber, the tubes comprising apertures within which the marijuana plant is supported with the roots occupying a root zone within the tube.

Walls of the growth chamber may comprise any suitable material, for example metal, plastic, composites and the like. Preferably, the walls comprise a light reflective material. Preferably, the walls comprise a plastic composite. The growth chamber may comprise a self-contained cooling and ventilation (HVAC) system including, for example, one or more air moving devices (e.g. fans, blowers, etc.), air conduits (e.g. tubes, ducts, etc.), air conditioners, air filters (e.g. carbon filters, HEPA filters, etc.), sensors (e.g. sensors for odor, humidity, temperature, pressure, etc.) and lamps for artificial illumination. The growth chamber may further comprise one or more access panels for service and maintenance of structures inside the growth chamber and for planting of marijuana plants.

Temperature and humidity, as well as pressure, may be monitored at various points in the growth chamber and may be managed in a root zone inside the plant support structure, stalk zone amongst the plants themselves and lamp zone at an upper section of the growth chamber where the lamps, and optionally lamp ballasts, may be located. The growth chamber may be designed to achieve a temperature gradient between a lower portion and the upper portion of the growth chamber so that only the plants themselves are maintained at an optimal temperature and anything else is simply maintained within permissible operating ranges but at significantly different, for example higher, temperatures than the plants.

Air may be introduced at any suitable location, for example proximate a base of the plants, not only to achieve the temperature gradient but also to ensure there is adequate air circulating around every plant to reduce the chances of mold and mildew growth. One or more structures for introducing a sanitizing agent (e.g. hydroxyl) into the growth chamber may also be included, preferably proximate the base of the plants, to deal with any accidental contamination of the plants. Airflow may be further beneficial for causing plant swaying and motion, which helps reduce dead air pockets as well as stimulating the plants to produce more fibrous stalks so they are more durable to handle, can support a heavy crop, and are less prone to wilting if undesirable conditions accidentally arise.

The cooling and ventilation system may operate mainly on recirculated air for efficiency and to minimize the amount of air being filtered at the inlet and outlet to the environment where contamination could enter or leave. The proportions of recirculated and new air may be adjusted automatically by variable speed air movers if desired.

Micro-climate Environment Measurements

Measurement of various parameters of the micro-climate and growth chamber permit feedback loops to a controller to control the parameters in order to optimize growing conditions for the marijuana plants and operational functions of the growth chamber. Measurements may be acquired by various sensors and the sensors send signals to the controller, which acts on the signals in a manner consistent with programming of the controller. Parameters and sensors involved in the measurement of the parameters may include, for example, the following.

Lamp Ballasts (Ballast Sensor). Lamp ballast sensors may be mounted on each lamp ballast. Lamp ballast sensors may be used in conjunction with temperature sensors in the upper section of the growth chamber to ensure that the HVAC system keeps the temperature in upper section of the growth chamber within acceptable limits. The lamp ballast sensors may also propagate alerts to the controller so that operators may be notified. Lamp ballast sensors may optically receive and translate status codes presented by the indicator LED in individual lamp ballasts in a non-intrusive fashion. Status codes may include, for example, normal, over-voltage, under-voltage, lamp missing or defective, lamp EOL approaching, ballast over-temperature and ballast start-up. In addition to or instead of lamp ballast sensors, a smart ballast may be used in conjunction with an optical sensor, and/or a temperature sensor may be used just to measure the heat sink temperature. Lamp ballasts may be located within or outside the growth chamber.

Air Temperature/Humidity (Temperature and/or Humidity Sensors). Air temperature and/or humidity sensors may monitor an upper limit of the vertical temperature and/or humidity gradient established in the growth chamber. Signals from the sensors may prompt the controller to operate the air moving devices and HVAC to help maintain the vertical temperature and/or humidity gradient, or may propagate an alert to the controller if conditions cannot be maintained. The temperature sensor may comprise, for example, a solid state sensor used to determine the temperature of a fluid or surface which may include both air and water. The humidity sensor may comprise a sensor used to measure water vapor level in air and in conjunction with the temperature sensor provide a reading of relative humidity. Temperature and/or humidity sensors, as well as other sensors, may be integrated into one sensor.

Barometric Pressure (Barometric Pressure Sensor). Barometric pressure sensors measure the pressure in air or other fluid at the sensor, preferably for measuring differences in pressure between pairs of sensors. Of especial importance is the difference in pressure between the micro-climate in the growth chamber and the environment outside the growth chamber so that the controller may be able to maintain a negative pressure in the micro-climate relative to the pressure outside the growth chamber.

Air Quality (Air Quality Sensor). An air quality sensor may be used to monitor the effect of an active smell control system (e.g. hydroxyl) on the air in the micro-climate. The air quality sensor may also be used as a ripening detector to measure how fragrant the marijuana crop is when the hydroxyl generator is turned off for a period of time. The air quality sensor is preferably located in the upper section of the growth chamber, preferably at a midpoint. The air quality sensor measures relative total concentration of a broad range of molecules having a broad range of molecular weight.

Exhaust Air (Air Quality Sensor, Light Gas Sensor). One or more sensors on an exhaust outlet of the growth chamber may monitor concentrations of contaminants in air exhausting from the growth chamber and compare the concentrations with background levels outside the growth chamber as well as levels in the micro-climate. The air quality sensor may measure relative total concentration of a broad range of molecular weight compounds in the air. The light gas sensor may detect impending filter effectiveness degradation by measuring relative total concentration of light molecular weight compounds in the air (e.g. hydrogen, methane, etc.)

Interior of Growth Chamber (Image Sensor). An image sensor and image processing software may be used to determine plant canopy height (scaled horizon line), plant foliage density (average color of plants and background), plant foliage color (normally green), where a tendency to yellow while growing indicates deficiencies (some strains go purple near harvest as well), distance of lamps from plant canopy and canopy defects (deviation from average in the canopy color or density can mean irrigation or ventilation issues which need investigation). The image sensor may be a conventional camera imaging sensor. The image may be processed down to a vertical series of pixels by averaging the red/green/blue (RGB) components of every pixel within the horizontal field of interest on each horizontal row. The field of interest may be determined by edge detection of a vertical marker strip on the background in a contrasting color. Horizontal marker strips in contrasting color may also be used to provide scale calibration of the processed image data, so sensor positioning is not critical provided the sensor is roughly pointed at the area of interest.

Plant Canopy (Temperature/Humidity Sensors). The temperature and humidity sensors in the plant canopy may be used to ensure that the area where the plant actually exists within the growth chamber is at the proper temperature and humidity. Other temperatures are simply incidental and are only controlled within the rating limits of equipment within them, not directly for the plants' needs. The temperature sensor may comprise, for example, a solid state sensor used to determine the temperature of a fluid or surface which may include both air and water. The humidity sensor may comprise a sensor used to measure water vapor level in air and in conjunction with the temperature sensor provide a reading of relative humidity.

Root Zone (Level Probes and/or Hygrometer, Temperature Sensor). A level probe in the root zone may serve as both a high level limit in a flood and drain cycle as well as being able to detect blockage in an individual plant support structure. The level probes provide a digital indication of whether or not liquid is present at the measuring point. A variation of the level probes may use a different probe connected to the same electronics to provide an indication of the moisture level of any media surrounding the roots. In general, the probes may monitor limits of liquid levels or may monitor to ensure that liquid is present in the correct location(s). Most of the probes may monitor upper limits for detecting a problem or to immediately stop whatever action is causing a rise in liquid level. Other probes may monitor lower limits to determine when to turn a pump off because there is no more liquid to pump. This can provide useful information to supervisory control systems for use in logical decision making in combination with other input variables. For example, a condensate/table accumulator undergoing a rapid change in the time taken to fill is likely indicative of a catastrophic leak in the water management system. The use of a combination of upper and lower limit level probes provides an early indication to the supervisory control system, which can then signal the pump to shut off or alternatively shut down the entire system and alert an operator. The temperature sensor provides an indication of the temperature in the root zone, which provides a signal to the controller for maintaining temperature in the root zone within operating specifications.

Irrigation Runoff Accumulator Upper (Liquid Level Gauge). The liquid level gauge in the irrigation runoff may be used to establish the time of concentration and pervious nature of the root zone by deriving the runoff hydrograph from known water levels and storage volumes. The liquid level gauge may be an ultrasonic transducer which measures the pulse return time of a ping to determine the distance from the gauge to the liquid surface.

Solution Preparation Subsystem (Monitoring and Adjustment)

The solution preparation subsystem may comprise one or more tanks for mixing and/or storing irrigation solution. The number of tanks may depend on the number of different kinds of chemical components, the chemical components being stored individually in separate storage containers. Each separate storage container for chemical components may further comprise a sensor (e.g. a scale) for measuring an amount of the chemical in the container, a metering pump for delivering a measured amount of the chemical component out of the container and associated conduits (e.g. lines, tubing). The conduits may feed into a flushing chamber, which leads to the tank through other conduits.

Monitoring sensors for monitoring levels of chemical components and other parameters may be located at any suitable location in the apparatus, for example in the one or more tanks, in a conduit that eventually leads to the growth chamber from the tank or in a conduit that eventually leads back from the growth chamber to the tank. Sensors may include, for example, temperature sensor, flow sensor, peroxide sensor, enzyme sensor, color sensor, conductivity sensor, pH sensor, dissolved oxygen sensor, and the like. Although water is preferably recycled, deionized water may be supplied to make up any losses in water. A purge drain may be included for when it may become necessary to empty the water from or dilute the water in the water management system.

Besides water, other chemical components may include, for example, nutrients, acid, alkali, trace elements, flavor additives, hydrogen peroxide, enzymes that facilitate plant processes for plant growth, sugars (e.g. glucose, sucrose), marker dye (e.g. organic dye), and the like.

Flow may be measured to ensure that irrigation solution is flowing past the sensors representing the state of the solution correctly. pH may be measured to determine acidity of the solution. Conductivity may be measured to derive Total Dissolved Solids (TDS) content of the solution. Dissolved oxygen may be measured to determine residual $O_2$ in the solution as an indirect measurement of peroxide level, reducing biological oxygen demand (BOD) with peroxide or just from aeration of the solution. A temperature sensor ensures that the temperature of the solution is maintained in a suitable range and also provides a calibration temperature for other sensors which require calibration. A colorimeter with a light source may be used to check the solution for any discoloration from algae, turbidity, undissolved solids, etc., and also to measure residual levels of enzyme or peroxide based on the rate of breakdown of a marker dye.

During operation at different phases of the life cycle of the marijuana plants, the solution preparation subsystem may have target levels for total dissolved solids (TDS), pH, dissolved oxygen saturation, BOD, and enzyme concentration. The target levels may be further broken down into desired compound proportions based on which chemical components contribute to the target. The solution preparation subsystem in a feedback loop with the controller may determine how much of which chemical component to add to compensate when the target levels are out of specification and then implement any required changes. Levels not only change due to plant uptake, evaporation, etc., but vary from "day" to "night" and may vary in ramp or other non-linear fashion within a growing cycle phase. The solution preparation subsystem may constantly and automatically determine the current target level and work to bring all measured parameters back into a desired range if deviation occurs. For example: if the pH is too low, alkali may be added; if the pH is too high, acid may be added; if the total dissolve solids (TDS) is too high, the solution may be drained and then deionized water added to the drained solution; if TDS is too low, nutrients and/or flavor additive may be added; if dissolved oxygen is too high, the solution may be drained and then deionized water added to the drained solution and a hold period implemented to stop recirculation of the solution for a period of time; if dissolved oxygen is too low, hydrogen peroxide and/or enzymes may be added, circulation rate increased and aeration implemented (if available); if enzyme level is too high, the solution may be drained and then deionized water added to the drained solution; and, if enzyme level is too low, enzyme may be added.

Flavor Additives

One or more flavor additives may be utilized in the solution preparation subsystem to provide a unique way of producing flavored marijuana by incorporating the one or more flavor additives into the plants during one or more plant growth phases. Some current strains of marijuana plants exhibit natural flavors similar to those of blueberry, cantaloupe, lemon, mint, grape, blue cheese, etc. However, there is a desire to further enhance such flavors and/or to introduce different flavors than are currently available. Current methods in flavoring tobacco involve adding flavorings after harvesting the plant, but these methods produce less than satisfactory results, and may not be legally permitted.

Flavor additives may be chemical compounds that in and of themselves impart flavors (i.e. flavorings), or may be building block chemicals that are metabolized by the plant to produce flavorings. Utilizing flavor additives during growth of marijuana plants provides for a number of possibilities as follows. Any one or combination of the following techniques may be used to achieve either greatly enhanced naturally occurring (in that strain) flavorings in the harvested product, and/or infuse the product (while still alive) with flavorings which do not occur naturally in that strain or at all in marijuana, while at the same time reducing concentration of those flavorings that impart undesirable flavors. The product may be, for example, a vendible portion of the marijuana plant (e.g. buds, leaves).

Levels of inherent natural flavorings in a marijuana strain may be enhanced by providing specific building block chemicals during a growth phase of the plants when the parts of the plant of interest are being formed. For example, flavor additives for the leaves may be given during the vegetative growth phase while flavor additives for buds may be given during the flowering phase. Examples of such flavor additives include potassium citrate, which is a building block for plant growth and citrus flavor, and ammonium or metal acetates, which are building blocks for plant growth and berry/grape flavors.

A plant may be able to produce or include flavorings based on two or more other chemical pathways utilizing natural flavorings already present or not present in the strain. By introducing natural flavorings, for example various sweet fragrant juices of fruit and other plants (e.g. simple sugars, orange juice, grape juice, beet juice, etc.) to the irrigation solution, which may be combined with enzymes or bacteria, a wide mix of compounds for use by the plant may be produced. Natural flavorings may be simply drawn along with the water up into plant tissue and remain there unchanged chemically, infusing the tissue with the flavor, which is particularly useful during a leaching phase of the plant growth cycle. When enzymes are used in conjunction with natural flavorings, the enzymes may break down the natural flavorings into building blocks for the plant to produce its own flavorings, which may or may not be the original flavorings. This is particularly useful during the vegetative and flowering growth phases.

Specific residual flavorings may be targeted for enhancement or removal. A plant works internally by osmosis. During the leaching phase of growth, traditionally plain tap water has been used to cause the plant to give up unbound metal ions back into the nutrient solution since the metal ions impart a bad taste to the product. Metal ions cannot be excluded from use altogether though, because the plant needs metal ions, for example potassium, to remain healthy. Yet excess metal ions, e.g. potassium, are undesirable. At the same time, there are desirable flavorings that can accumulate in plant tissue as compounds but are not a part of the living plant itself, which are desirable to have remaining in the plant tissue. In the present invention, the irrigation solution during the leaching is based on deionized water in which trace metal ions are already removed. Further, irrigation solution may be dumped and refreshed during the leaching phase; therefore, undesirable metal ions are continuously drawn from the plant and diluted in the irrigation solution for improved removal. At the same time, to reduce removal of desired flavor additives, the concentrations of flavor additives may be maintained at higher levels in the irrigation solution than in the plant. However, because metal ions are not needed during the leaching phase to promote plant growth and metal ions impart a bad taste to the final product, the form of the flavor additives may be switched to exclude metal ions. For example, potassium citrate may be switched to citric acid and the pH carefully balanced with an alkali that does not comprise a bad tasting metal ion.

Enhanced uptake of the flavor additives may be obtained by altering other parameters. The growing environment itself may be managed to induce the plant to draw in more liquid and promote a more vigorous ion exchange with the irrigation solution by any of the following methods individually or in combination: decreasing "day" humidity to promote transpiration; increasing "night" humidity to encourage liquid travel down the plant at night; increasing "day" temperature to promote transpiration; increasing air flow rate adjacent to the plants to promote transpiration; increasing "day/night" light change frequency to circulate liquids within the plant as vigorously as possible; providing a final very long "day" to draw up one last time any flavor additive desired as a residual element of the plant tissue; increasing irrigation cycle frequency when transpiration is promoted; and, adjusting pH of the irrigation solution to promote or retard migration of different compounds into or out of the plant at different times.

Some examples of flavor additives include: citric acid and/or salts of citrates and/or esters of citric acid (e.g. ethyl citrate) for lemon flavor (like the strains lemon haze, lemon kush); menthone or precursors thereof for mint flavor (like the strains critical kush); acetic acid and/or salts of acetic acid and/or esters of acetic acid (e.g. ethyl acetate) for berry flavorings (like the strains blueberry kush, bluegoo, grape); and, sweetness building blocks (e.g. simple sugars—glucose, sucrose, etc.), which at high enough levels result in chocolate or caramel flavors after combustion or heating. Any mixture of flavor additives may be employed.

Enzyme Measurement

Measurement of enzyme levels in the solution preparation subsystem is a unique way of monitoring and controlling marijuana plant growth. Enzymes are used as part of a nutrient regime for various reasons when growing marijuana plants. Some uses of enzymes include, for example, cleaning roots of dead plant material and digesting dead plant material into compounds the plant can use for growth instead of the dead plant material contributing to the BOD (biological oxygen demand) of the solution. As a result, the root mass may be submerged in irrigation solution for longer periods of time without becoming anaerobic. This can be more or less important depending on the amount of time roots spend submerged in liquid and varies by the hydroponic method utilized. Enzymes are also used to break down larger molecules in the irrigation solution into smaller ones which the plants can more readily absorb.

There is no easily applied direct way of measuring enzyme concentration in the irrigation solution with an electronic sensor in the manner of pH or conductivity. The amount of enzyme needed in the irrigation solution varies with conditions, but measurement of residual enzyme level and maintaining a high enough residual enzyme level to have the desired effect is what is important. In the present water management system, a marker dye may be used to tint the solution a color which spectrally does not coincide with colors already occurring in the irrigation solution. Since the irrigation solution is high in nitrates and phosphates and passes by bright lights during its irrigation journey, potential to grow algae is high. Contamination with algae would impart a green tint to the solution. Therefore, a marker dye may be chosen that does not coincide spectrally with green. The marker dye may comprise an organic dye, for example an organic dye which would impart a tint to the solution in the blue and/or red ranges. A naturally occurring marker dye is preferred. A particularly preferred marker dye comprises beet juice. Beet juice is a natural substance having no issues with its use on a food/medical crop. Beet juice also contains sugars which the enzymes can digest and is beneficial as a nutrient in the irrigation solution in general. Beet juice is also readily available on an industrial scale at low cost.

To measure residual enzyme levels in the irrigation solution, advantage is taken of the fact that the enzymes digest the marker dye. The rate of breakdown of the marker dye is correlated to the level of residual enzymes. To make the measurements, a colorimeter (e.g. a spectrophotometer) set at an appropriate wavelength for detecting light absorbed by the marker dye may be illuminated through the translucent irrigation solution by white light. When a known concentration of marker dye is introduced to the irrigation solution, a baseline absorption at appropriate wavelengths may be established. The rate of change of the absorption may then be monitored, which is proportional to the residual enzyme level. Adjustments may be made to the amount of enzyme if necessary taking into account the known total liquid volume of the system for dilution.

Solution Delivery Subsystem (Sanitization, Root Management and Root Temperature)

The solution delivery subsystem may comprise one or more pumps fed from the one or more tanks, preferably via one or more filters (e.g. particle filters). The one or more pumps may pump irrigation solution to a solution delivery header in or proximate the growth chamber. A pressure monitoring sensor, preferably located proximate a furthest point in the delivery header, may provide feedback to the controller to control the one or more pumps to adjust the pressure to a desired level in order to compensate for solution losses in conduits and a variable number of growth chambers, which may be irrigated at any given time.

The delivery header may be in fluid communication with the growth chamber through one or more valves, for example one or more automated solenoid valves. Opening of the one or more valves may follow timing patterns set by the controller and may vary widely depending the current growth phase of the marijuana plants, as well as other directives, for example sanitizing, root management, nutrient provision and the like.

The valves may feed distributors that are in fluid communication with sprayers (e.g. nozzles) within a root zone. Irrigation solution may be provided to the sprayers at a pressure high enough to result in a mist in the root zone which aggressively saturates the root ball of the plants. By varying cycle timing and the chemical components in the irrigation solution, the size of the root balls may be managed for a desired amount of roots on the plants. As a result, nutrients may be more efficiently utilized to grow the top (e.g. stems and leaves) of the plants and root length may be controlled to avoid physically plugging the root zone. Further, less root mass means less disposal cost per plant and smaller root masses are easier to keep from becoming anaerobic and having undesired effects.

The irrigation solution may be allowed to drain to a collection chamber below the root zone where the runoff rate and stored volume measured. Runoff rate and stored volume in a collection chamber may be used to derive the root mass present at any given time based, in a manner similar to how storm water runoff analysis is done in a city storm sewer system. When the stored volume of irrigation solution exceeds a set amount, the stored irrigation solution may be pumped back into a second header leading back to the one or more tanks, preferably through a filter (e.g. a particle strainer). The second header may further comprise a sterilization module (e.g. an ultraviolet (UV) treatment module) to sanitize the irrigation solution.

The solution delivery subsystem may be generally referred to as aeroponic, however this subsystem has several distinctions from aeroponic systems. Another system commonly referred to as "flood and drain" comprises feeding irrigation solution on a timed cycle to the root mass of the plants (with or without soil or pseudo-soil) so that the root mass is completely surrounded by solution for a fixed period of time and then the solution is allowed to drain away. The present solution delivery subsystem may also operate in a "flood and drain" mode where the root zone is allowed to fill instead of the solution being immediately carried away. The "flood and drain" mode may be used for sanitizing the roots, or for any other reason desired by an operator. The "flood and drain" mode may also be used under emergency conditions to mitigate a power failure. Aeroponic systems are vulnerable to power outages, which may result in the roots drying out causing permanent damage to the roots. In the event of a power failure in the present solution delivery subsystem, there is enough emergency power to open valves and allow the root zones to accumulate enough water to keep the roots wet, so that the plants can withstand extended power outages with no damage.

The solution delivery system may operate in any of the 6 basic hydroponic irrigation modes (Wick, Drip, Flood and Drain, Nutrient Film, Aeroponic and Floating) simply by changing the nozzle type and position (spray, drip or open, and between or at plant sites), and switching the location and type of the level probes. (analog or digital, above, in or below the root mass). The reason for switching the base mode of hydroponic operation physically would be operator driven based on historic preferences or pairing to a specific plant strain requirements.

The solution delivery subsystem may also comprise one or more chillers, which maintain the temperature of the irrigation solution, which in turn controls temperature in the root zone. The solution delivery subsystem and solution preparation subsystem cooperate to form at least a major part of the water management system.

Root Management

Root management including the ability to control root ball (root mass) size is a particularly useful aspect of the solution delivery subsystem, and is in some ways coupled to microclimate management. There are various reasons for wishing to control the size of a plant's roots including reducing chance of plugging the root zone, allowing easy removal of the plants from the plant support structure, reducing disposal cost of plant matter, using nutrients more efficiently to bias growth to marketable parts of the plant, accelerating growth of the plant by optimizing uptake abilities and creating a more robust plant earlier in its life. The process may be used to quickly grow roots to a desired size and then retard further growth, dedicating plant energy to the above ground portions of the plant for more efficient and faster growth.

In order to control root growth rate a number of different variables may be employed. The controller may be programmed with a template for a given marijuana plant strain as a starting point with a recipe on how to most efficiently obtain the correct root mass. If the system is not meeting programmed targets, an operator may override any of the variables and change the growth regime. Variables to be controlled in root management may include, for example, one or more of "day/night" light cycle timing, irrigation timing and duration, aeroponic and flood/drain options, concentration of nutrients specific to root development, concentration of nutrients specific to non-root development, sanitization via peroxide or enzymes, oxygenation level of the irrigation solution via peroxide or aeration, BOD reduction via peroxide or enzyme, temperature and humidity in the growth chamber, airflow velocity adjacent to the plants and pH of the irrigation solution.

Controlling so many variables related to the growing conditions for the plant benefits from having a feedback loop for at least two reasons. First, it is important to be able to determine the actual value of some of the parameters to be varied. For example, when adjusting the pH, the irrigation solution may be mixed and continuously sampled with a pH sensor to determine whether the action taken had the desired result. In another example, when varying the speed of a fan to vary the airflow adjacent the plants, barometric pressure may be monitored in the growth chamber to ensure that the intended result actually happens.

Second, it is important to measure how well the measures being taken are affecting the outcome of targeted root growth. In traditional watershed analysis, expected runoff characteristics are computed based on the vegetation and characteristics of the watershed. In the present root management system, vegetation (i.e. root characteristics) may be predicted from runoff characteristics, for example by measuring shape of a runoff curve from an irrigation cycle of known intensity and duration, and how that changes over time. Therefore, runoff characteristics of irrigation solution draining from the root mass are used as feedback information to alter variables that affect root growth.

Baseline parameters of a runoff hydrograph may be established based on an empty (of roots) root zone with fresh transplanted seedlings or clones. Runoff characteristic of particular interest may include, for example:

Time of concentration (time offset from start of irrigation cycle to the maximum peak of the runoff curve). Time of concentration provides a direct indication of how massive the root balls are and how long the root balls take to saturate with water before everything being applied simply runs off. Time of concentration is also an indicator of optimal "on"

times for irrigation by taking into account travel time from the furthest point of gravity flow.

Peak flow (maximum level of the curve). Peak flow is inversely proportional to root mass and may be employed in combination with time of concentration.

Integral value of the curve (area under the curve or total flow). The difference between integral value of the curve and how much liquid was introduced is an indication of the structure of the root balls and whether they are porous and hold water or impervious and shed all the liquid applied to them quickly.

Tangential time offset (time after which there is essentially zero flow). Tangential time offset is proportional to root mass as well as the coarseness of the root structure and how well surface tension holds liquid in the root structure. Tangential time offset is also important in determining the optimal time between irrigation cycles, which is adjusted dynamically.

As the feedback sensing provides data during root growth, the variables above are adjusted by the controller automatically to achieve the goals without wasting resources. For example, as the tangential offset time starts to increase, the controller automatically backs off the aggressiveness of irrigation when in a root building phase of growth to force the plant to produce more roots to search for nutrient. When in a root retarding phase the opposite action would take place automatically. As monitoring starts to indicate liquid being impounded by the root structures, it is important to become more aggressive with managing oxygen levels in the irrigation solution to keep the root ball healthy. Too much oxygen too early damages and stunts the roots. However later it is beneficial to deliberately oxygenate aggressively once the root mass is at the desired size to curb new growth and to keep the root mass from becoming anaerobic. The system manages roots through monitoring and dynamically adjusting the regime of parameters for growth.

Odor Control Subsystem

Ripening marijuana buds have a very distinct odor, which some people find unpleasant. Health Canada requires no odor emissions at all from a marijuana production facility. A subsystem for odor control may be provided, which treats the air within the micro-climate, filters the air released from the micro-climate, monitors the effectiveness of both these processes, takes steps to mitigate interruptions of these processes and alerts an operator to specific problems with the apparatus if they occur. The odor control subsystem may comprise the following parts: an outdoor on-site weather station, a building envelope, one or more growing micro-climates, building envelope intake air filtration, building envelope exhaust air scrubbing, micro-climate intake air conditioning and filtering, micro-climate exhaust air scrubbing, micro-climate management controllers, building envelope management controller, system management back end, alerts and alarms and system operators.

The odor control subsystem may comprise a number of layers of protection against not only odor escape, but also against entry of undesirable substances from the outside environment. Generally, the odor control subsystem may comprise a micro-climate in an enclosed growth chamber, preferably a plurality of growth chambers, situated within an interior space of a building or like structure to form a facility where growing the marijuana takes place.

The growing environment may be isolated inside one or more growth chambers maintained at negative pressure with respect to the building envelope containing it. All air leaves the growth chambers via air filters (e.g. carbon filters) to remove odors. Should the micro-climate in the growth chamber be breached for any reason, building air will flow into the growth chamber rather than odors flowing out. Air entering the growth chambers may pass through an air filter (e.g. HEPA filter) to remove airborne contaminants.

The building air itself may also be scrubbed with air filters (e.g. carbon filters) when exhausted and HEPA filtered for incoming air. The building will normally be at slightly positive pressure with respect to the outside environment. This ensures that the building envelope contains only clean air filtered on the way in and any leakage is towards the outside.

However, should a problem be detected with any of the filters on the micro-climate, or some other form of breach, the building envelope may change modes to become negative pressure with respect to the outside environment, ensuring all air leaving the building passes through filters and no air leaks out any other place.

In another mode of operation of the odor control subsystem, when external contaminants are detected the building may temporarily switch to zero outside air mode to avoid drawing anything in which might contaminate the crop. Contaminants may arise from, for example, nearby pesticide spraying, accidental chemical spills, fires, air exhaust from nearby structures, etc.

Functions of the odor control subsystem may be managed via a number of controllers which have some redundancy so that other parts of the overall subsystem may compensate for and minimize impact of equipment failure. A central controller may oversee operation of individual controllers on the growth chambers and may also be responsible for sending the appropriate alerts or alarms related to the operation.

Alerts may ensure that maintenance is carried out when required, for example filter changes, before a problem develops. Alerts relate to situations that need attention but are not critical to deal with immediately. Alerts may be shown on a status screen and provided to (e.g. e-mailed to) an appropriate operator for attention during a next scheduled maintenance period.

Alarms are the more urgent counterpart of alerts and require operator intervention immediately to correct a deviation. Alarms may relate to situations like filter breaches, atmospheric pressures out of range, fan failures, a contaminant detected outdoors, etc. The subsystem may attempt to automatically compensate where possible, for example by switching the building envelope from positive to negative pressure if a micro-climate fails.

In general, the odor control system attempts to prevent any odor release from the building, while still attempting to maintain as normal an operation as possible.

Outdoor On-site Weather Station

One or more outdoor on-site weather stations may monitor and record outside air conditions including temperature, humidity, wind speed and direction, odors, other gases, barometric pressure and other inputs. The outdoor on-site weather stations provide inputs to the controllers to permit efficient operation of the HVAC system, proper maintenance of the building envelope relative pressure and anticipation of indoor thermal lag based on outside conditions. Outside conditions may be monitored to provide an opportunity to reduce entry of contaminants into the micro-climates at levels or types of contaminants which the normal intake air filtration cannot handle. Further, surrounding air outside the building may be monitored for the possibility that odor containment has failed and odors are being released. At the same time, based on wind speed and direction it can be established whether the odor is from the marijuana growing facility or originating off-site, which is important in dealing with any odor complaints. The exact conditions at the time of a complaint may also be determined (wind speed and direction, temperature, etc.) so that dispersion calculations may be performed to determine whether the complaint has merit.

Building Envelope

The building envelope is a second layer of protection against odor release or contaminant ingress. The building envelope provides a controlled buffer between the micro-climates and the outside environment.

Growing Micro-Climates

The micro-climate is a first layer of protection against odor release and provides a growing environment around the marijuana plants which may be tailored to reduce odor generation. By reducing odor generation at the level of the growing plants, the volume of contaminated air may be reduced, and fast changeover through filters may ensure that the concentration of odor is further minimized. The micro-climate may be maintained at negative pressure with respect to the surrounding space to further reduce escape of odor.

Building Envelope Intake Air Filtration

HEPA particulate filters including sensors which can detect a filter breach and a filter nearing the end of service life may be included in the building air intake. The air may be moved by a fan, preferably a variable speed fan, which may be operated as part of a building envelope atmospheric pressure control system.

Building Envelope Exhaust Air Scrubbing

Absorptive filters (e.g. carbon filters) may be employed to remove organic compounds from the air stream. The filters may have sensors to detect a filter breach, sensors on outlets, to detect odor pass-through and/or sensors to determine when a filter is nearing the end of service life. Air moving through a filter may be driven by a fan, preferably a variable speed fan, which may be part of the building envelope atmospheric pressure control system.

Micro-climate Intake Air Conditioning and Filtering

HEPA particulate filters including sensors which can detect a filter breach and a filter nearing the end of service life may be included with the growth chambers. The air may be moved by a fan, preferably a variable speed fan, which may be operated as part of a micro-climate atmospheric pressure control system.

Micro-climate Exhaust Air Scrubbing

Absorptive filters (e.g. carbon filters) may be employed to remove organic compounds from the air stream. The filters may have sensors to detect a filter breach, sensors on outlets from the micro-climate to detect odor pass-through and/or sensors to determine when a filter is nearing the end of service life. Air moving through a filter may be driven by a fan, preferably a variable speed fan, which is part of the micro-climate atmospheric pressure control system.

Micro-climate Management Controllers

Micro-climate management controllers associated with each growth chamber may be responsible for maintaining the micro-climate within the associated growth chamber, so that failure of one may not affect the others. The micro-climate management controllers may monitor and maintain specified conditions including, for example, lighting, air circulation, air pressure, air quality, temperature, humidity, feeding patterns and the like. The micro-climate management controllers may take direction from the management back end, and report all of sensor data back for recording as well.

Building Envelope Management Controller

A building envelope management controller may be responsible for maintaining conditions in an interior space outside the micro-climates but within the building. Conditions may include, for example, air pressure, temperature, and humidity. The building envelope management controller may also take direction from the system management back end and report all sensor data back for recording.

System Management Back End

The back end of the odor control subsystem may be driven by a database. All the incoming sensor data may be recorded for future reference. Rules for the logic of the odor control subsystem and "programs" for growing cycles may be stored. Set points may be provided to the micro-climate management controllers and building envelope management controller. The micro-climate management controllers and building envelope management controller may then operate within that set of instructions until the set points are changed as the system changes to a different mode of operation, or corrects for some ongoing changing condition, or in response to an operator manually making a change.

All management functions may be accomplished by interacting with the system management back end through a user interface, which may be remote with access provided through a network connection, for example through the Internet.

When signals from the sensors change, a rule engine may be processed to determine whether any modes of operation need to be changed, or if any conditions have crossed a threshold constituting and alert or an alarm.

Alerts and Alarms

Alert and alarm conditions may be driven by rules in the management back end. Alerts are non-critical and may be pull or push driven to the operators based on individual preferences. Alerts may be viewed as a list to deal with at the start of a shift, may be e-mailed or SMS messaged individually or a combination thereof. If alerts are not dealt with in a timely manner, the alerts may escalate to alarms which demand more immediate attention.

Alarms may be critical in nature and require immediate attention. Alarms may be dispatched to an operator by any suitable urgent method, for example via telephone, SMS messaging or with an Internet-based pull driven monitoring application according to operator preferences. If alarms are not dealt with or acknowledged during an initial notification window, the alarms may be automatically escalated to notify other operators.

Equipment related to odor control may be equipped with one or more status lights, preferably multicolored. Changes in the status lights may be used to indicate various operation modes and urgency of any non-optimal conditions. Status lights may form a first line of defense to on-site operators circulating to alert the operators to a problem even if some other operator may have received a notification but has not responded to the problem.

Status of the odor control subsystem may be viewed or operation altered from user interfaces, for example control boards or personal computers on-site or remotely from control boards, personal electronic devices (e.g. cell phones) or personal computers. Remote access to the odor control subsystem may be accomplished through a network connection, for example through the Internet.

System Operators

System operators may be provided with training on functioning and maintenance of the odor control subsystem, including data interpretation, responding to alerts and alarms and recognizing anomalous conditions that the controllers may not be programmed to manage. Standard operating procedures (SOPs) may be established in connection with identifying and managing routine conditions and explaining what to do in circumstances not covered by SOPs. Spare parts and consumables may be available to operators at all times on-site to permit timely maintenance and repair.

Method of Application

As described above, the odor control subsystem may comprise one or more of the following. Air quality sensors may be located in the air outside the growth chambers, within each growth chamber and at an exhaust air outlet from each growth chamber downstream of an air filter (e.g. a carbon filter). Barometric pressure sensors may be located in the air outside the growth chambers, within each growth chamber and at the exhaust air outlet from each growth chamber upstream of the air filter. Light gas detectors may be located at the exhaust air outlet of each growth chamber. A barometric pressure sensor may be located in a supply air duct between a supply fan and a diffuser of each growth chamber. An exhaust fan, preferably variable speed, which pulls air from the growth chamber through the air filter (e.g. a carbon filter) before being exhausted. A hydroxyl generator located in a recirculation duct from the growth chamber. A supply air fan, preferably a variable speed fan, which pulls in a combination of return air from the growth chamber and a portion of air from outside of the growth chamber, and which introduces the air into the growth chamber, preferably through a diffuser. One or more access ports in the growth chamber for operator interaction with contents of the growth chamber during operation. An air filter (e.g. a carbon filter) may be located in the exhaust stream. A HEPA filter may be located in an intake air stream entering the growth chamber.

During early phases of growth the marijuana plants do not generate much odor. Airflow through is balanced by varying the speed of the fans to create a slight negative pressure within the chamber as compared to pressure outside the growth chamber to ensure that odors do not leave the chamber. An air stream leaving the chamber has one route out, that is, though the air filter, which removes odor-causing compounds from the air stream. If the pressure difference from inside to outside the growth chamber drops at any time, perhaps indicating that an access port is open, the speed of the exhaust fan may be increased to try to maintain the pressure difference and contain odors in the growth chamber.

If the pressure difference from outside air to the exhaust fan pressure sensor deviates from a known clean air filter/fan speed curve in a significant manner, one of two reportable conditions may have occurred. If the pressure is drifting higher than the curve over time, the air filter may have become physically plugged and needs to be replaced. If the drop is significantly less, the air filter may be either breached or the exhaust fan performance has degraded.

Similarly if the supply duct pressure sensor/growth chamber difference deviates significantly from a known diffuser/fan speed curve, two reportable conditions may have occurred. Less of a pressure difference is likely a result of a diffuser breach or degraded fan, and more of a pressure difference is likely a result of a blockage.

A third set of differences may be taken across the supply fan pressure sensor and the air pressure sensor outside the growth chamber. Similarly, pressure difference changes may be a result of blocked or breached filters.

In all cases, an alert may be provided to an operator. Multiple pressure differences out of range at the same time may be used to isolate which of the possible problem conditions is present where there is more than one problem.

As the marijuana plants mature and begin producing odors, two points of air quality measurement may be compared to determine if treating the air within the growth chamber with hydroxyl ions is necessary to reduce the odors compared to the air in the rest of the interior space of the building. The hydroxyl generator is turned on when the difference between the sensors reaches an unacceptable threshold and turned off again when the difference has become less than a return set point. The hydroxyl generator may also be used periodically even if no air quality issues are detected in order to sanitize surfaces in the growth chamber. This is a combination of timed events and also immediately following every time one of the access ports is opened, which means contamination could have been introduced by touch or by unfiltered air being drawn into the growth chamber through the access port. Such precautions also permit addressing minor leaks which may bypass the HEPA filter bringing in contaminated air that might contribute to mold or other undesired organic growth. Having a high contaminant reading from air quality sensors in the growth chamber or turning on the hydroxyl generator without seeing a corresponding drop in detected contaminants to acceptable levels within a given time may be an indication of failure of the hydroxyl generator, which is also a reportable condition. The increasing need over time for the hydroxyl generation cycle may be a direct indication of product ripeness and this data may be used by other subsystems to take appropriate actions.

Traditional marijuana growing apparatus that use carbon filters are limited to reactively changing the filter when smell becomes a problem, or simply changing the filer on a preventive maintenance cycle. The present invention provides at least two advantages over traditional apparatuses. First, there may be an air quality sensor in the exhaust air stream, which may be used to evaluate the exhaust from the growth chamber compared to the air in the growth chamber and the air in the interior space of the building to ensure that effective contaminant removal is taking place. Second there may be a light gas sensor in the exhaust air stream. The light gas detector takes advantage of a principal of the way a carbon filter works. When the filter is empty, molecules of all sizes and weights are captured in pores of the filter. As the filter starts to reach its capacity larger molecular weight molecules continue to get captured in the pores, however lighter weight molecules pass through the filter and molecules previously captured in the filter may become dislodged. As a result, a rise in concentration of light molecules in the exhaust air downstream of the filter occurs when the filter starts to lose effectiveness. The light gas detector detects the rise in concentration of light molecules, and may send a signal to the controller to provide a filter change alert to an operator. The filter change alert is pre-emptive since there is no reliance on detecting odors (heavier molecules) passing by the filter in order to determine that it is time to replace the filter.

In addition to alerts, automatic problem mitigation is possible. An example is described above is where the speed of the exhaust fan may be increased when an inadequate pressure differential is detected from outside to inside the growth chamber. In another example, if breaches in either of the filters are detected fan speed may be automatically reduced accounting for other constraints such as maintaining temperature and the hydroxyl generator may be turned on to constantly sanitize incoming air and try to neutralize any odors before they are exhausted. In another example, if a fan failure is detected, fan speed of another fan may be increased to maintain as much air circulation as possible. Mitigation measures may be designed to provide an operator with time to react to the alert, preserve the crop, and control odors under non-ideal operating conditions.

Environmental Awareness Subsystem

Information about an external environment may be gathered and integrated into operational parameters of the other subsystems. Data concerning various factors, for example real time power rates and weather warnings may help lower operation costs and mitigate a potential power failure by temporarily switching from aeroponic to flood and incomplete drain operation until the threat has passed. Further, as part of a garden management server and power distribution system all overall power and water usage may be measured in real time and coupled with real time rates to provide an operator a real time estimate for minute-by-minute costs as well as overall cost of a crop.

Furthermore, another aspect of environmental awareness is the macro-climate environment the micro-climate is contained in. The micro-climate is rated for operation up to certain worst case macro-climate conditions, but there is a possibility the macro-climate will exceed the worst case conditions. The system may compensate where possible by making adjustments such as a longer night period, colder root zones, etc. to try to either prepare for a coming anomaly or compensate during one, extending the growing cycle at the expense of maintaining yields or preventing plant damage.

Control System

The marijuana growing apparatus and facility may be controlled by one or more control systems. Elements of the apparatus and facility may be controlled separately or control of one or more of the elements may be integrated together. Integration of control advantageously permits using feedback loops between elements and/or subsystems to provide automatic control over operations.

The control system may comprise one or more of micro-climate management controllers for each growth chamber, building envelope management controller, a system management back end, sensors and an electronic communication infrastructure electronically linking the controllers, sensors and the system elements (e.g. fans, pumps, valves, lamps, air conditioners and the like that operate the system. Micro-climate management controllers associated with each growth chamber may be responsible for controlling the subsystems of the associated growth chamber, including controlling a water management system. The building envelope management controller may be responsible for maintaining conditions in the interior space of the building outside the micro-climates but within the building. The system management back end may be driven by a database that contains rules for the logic of system and "programs" for operating the systems. Sensors may provide raw data to the system management back end and the electronic communication infrastructure electronically connects the controllers, back end and sensors so that the parts of the control system may interact.

The control system may comprise a central controller that coordinates all of the other controllers. The central controller may be a separate controller or may comprise one of the controllers employed to operate a subsystem. For example, the building envelope management controller may also serve as a central controller. The central controller may process signals from various sensors and coordinate sensor signals from disparate subsystems to provide feedback instructions to one subsystem based on a signal from a different subsystem. Further, the central controller may centrally implement parameter set points to a plurality of micro-climate management controllers at each growth phase of the marijuana plants based on a collective analysis of the information obtained from the sensors of all of the growth chambers.

Further, the central controller may integrate control of a plurality of growth chambers with control over the building envelope so that information collected from building envelope operations may be used to inform decisions on how best to control growth chamber and water management system operations.

Controllers may comprise a computer, an output device and an input device. The computer may comprise a microprocessor for controlling operations and a non-transient electronic storage medium as part of the system management back end for storing information about growing conditions, operational parameters, sensor data, actions undertaken, and/or for storing computer executable code for carrying out rules or instructions for implementing the method. The computer may further comprise a transient memory (e.g. random access memory (RAM)) accessible to the microprocessor while executing the code. A plurality of computer-based apparatuses may be connected to one another over a computer network system (e.g. in an intranet, over the internet or a combination thereof) and geographically distributed. One or more of the computer-based apparatuses in the computer network system may comprise a microprocessor for controlling operations and a non-transient electronic storage medium for storing information about growing conditions and operational parameters, and/or for storing computer executable code for carrying out rules or instructions for implementing the method, and the computer-based apparatuses in the network may interact so that the marijuana growing apparatus and/or facility may controlled from a remote location. The output device may be a monitor, a printer, a device that interfaces with a remote output device or the like. The input device may be a keyboard, a mouse, a microphone, a device that interfaces with a remote input device or the like. With a computer, the growing conditions and operational parameters may be a graphical representation displayed in the output device. Input/output devices permit operator access to the controllers so that programming changes may be implemented manually. There is also provided a computer readable non-transient storage medium having computer readable code stored thereon for executing computer executable rules or instructions for carrying out the method.

The control system may further comprise human system operators. System operators may perform supervisory roles to ensure that the automated subsystems are performing correctly. System operators may also perform non-automated operations, maintenance and repair. System operators may be provided with training on functioning and maintenance of the apparatuses, system and facility, including data interpretation, responding to alerts and alarms and recognizing anomalous conditions that the controllers may not be programmed to manage. Standard operating procedures (SOPs) may be established in connection with identifying and managing routine conditions and explaining what to do in circumstances not covered by SOPs. Spare parts and consumables may be available to operators at all times on-site to permit timely maintenance and repair.

To assist operators, the controllers may be programmed to provide alerts and alarms connected with various subsystems based on data received by the controllers from the sensors. Rules programmed into the control system driving the operation of the various subsystems not only dictate the desired levels of parameters and how to correct for deviations but they also define what are warning and critical levels when a parameter deviates and cannot automatically be corrected. Any parameter of the apparatus, system or facility may have an associated rule setting such desired levels and providing corrective actions, alerts and/or alarms. Many proactive problem warnings center on a deviation from an established pattern from the sensors the system previously exhibited without a change in the operational parameters. The deviation may be related to an individual parameter versus time, or to a parameter within a group acting differently under the same conditions at the same time. Alerts and alarms previously described in the context of particular subsystems may be generalized to apply to any part of the overall system.

Operations may be driven by a series of prioritized rules which may be re-evaluated every time inputs change. Decisions may be made on how to adjust any of the targets set for the controllers for the subsystems.

The controllers may be programmed to respond to sensor data to automatically adjust system parameters to accommodate changing conditions in the building, micro-climate or any other part of the apparatus, system and facility. In particular, growth phase management of the marijuana plants is an important aspect to control and requires a comprehensive set of rules. The rules permit comparison of system wide parameters to historic data to determine when to switch from one growing phase to the next.

Each controllable aspect (lighting, nutrients, temperature, etc.) has target levels to maintain. Target levels vary according to application types (how a parameter is changed over time) during "day" and "night" time periods and during each growth phase. Depending on how the marijuana plant originated and the purpose of the plant, the plant may or may not go through all phases. The terms "day" and "night" refer to periods of light and dark to which the marijuana plant is exposed, which do not necessarily sum to 24-hour real-time periods.

For example, historic and current data on root growth may be available for the root management system, which is representative of the plant below "ground" level, so the phases concerned with root growth may proceed to a next stage when certain conditions are achieved. Historic data for the upper portion of the plant (e.g. stem, leaves, etc.), for example canopy height and foliage density, may be available from the imaging system, so when certain targets are achieved the growing regime may move onto a next phase. Historic and current data on relative strength of the odor emissions may be available from sensors in the odor control subsystem, and such data correlates to maturity of plant buds providing the ability to determine when to switch from flowering to leaching phases.

The growth phases of a marijuana plant are described below. The way in which rules would be implemented by the controllers to manage the apparatus, system and facility at each phase may be determined from the plant's requirements at each phase and the available controllers, sensors and other system elements.

Seed is the initial phase of a plant grown from seed, which is a starting point for tracking the plant through its life.

Cutting is a source of a clone taken from a host plant and marks the point at which a new individual plant is defined. A cutting generally comprises a leaf and stem with no roots, and is the start of tracking a new plant.

Seedling is a first growth phase of a plant grown from a seed and comprises initial roots, a stem and one or more leaves. Growth in the seedling phase generally requires high nutrient levels, high humidity, and subtler lighting than later vegetative phase.

Clone is a first growth phase of a plant grown from a cutting, and includes initial roots, a stem and one or more leaves. Growth in this phase generally requires high nutrient levels, high humidity, and subtler lighting than later vegetative phase.

Pre-Veg Toughening is a phase of development where the growing environment is gradually changed from a cloning or sprouting environment (generally high humidity around the complete plant (roots and leaves) inhibiting transpiration) to an environment where only the roots of the plant are moist and the upper vegetative portions of the plant are allowed to transpire since water loss and dehydration has been stabilized by enough root mass to support the plant's liquid needs. The plant toughens and minimizes the shock on the plant when it is transplanted to the micro-climate growing environment from a propagation environment. The purpose of this phase is to speed up the overall growth cycle by eliminating or minimizing the transplant shock phase of growth.

Transplant Shock is an undesirable phase of growth which is desirable to eliminate as much as possible, since transplant shock is a waste of time and resources. Pre-veg toughening reduces transplant shock significantly, however a period of more intense irrigation and higher permitted humidity, etc. may still be required to reduce the shock to the plants and help the plants recover more quickly. This may be the first phase of growth where plants reside in the micro-climate.

Root Building is a phase where the root mass is quickly grown to a desired size where the plant is capable of quick uptake of nutrients so that the composition of the chemical components in the irrigation solution may be altered to move into the next phase. The root building phase generally has a less aggressive irrigation schedule with more root formative components in the irrigation solution to make the roots search for nutrients and focus the plant's energy to the roots.

Vegetative is a vertical growth phase of the plant. Root mass may be managed during this phase by altering the chemistry of the nutrients to favor green portions of the plant (stem and leaves), and changing to a more aggressive irrigation schedule so the roots no longer have to extend to find nutrients. Lighting schedules may be employed to represent "summer" to the plant. Roots and root zones may be regularly sanitized to prevent the formation of algae or other microbes since the lighting and nutrient conditions favor algae and other microbe growth as well.

Flowering is a production phase of the plant corresponding to "late summer or autumn". Aggressive irrigation may be maintained, temperatures lowered and light cycles shortened to convince the plant to put all growth energy into producing flowers and fruit. Color of the light may also be changed to simulate changing angle of natural sun. Nutrients may be changed to a flowering specific chemistry. Some of the types of flavor additives may be used.

Leaching/Flavoring phase does not correspond to a natural phase of the plant life cycle. The purpose of leaching/flavoring is to permit natural leaching or removal of any compounds used in the nutrient solution which may impart an undesirable flavor to the finished product. This phase works similar to osmosis where ions travel from an area of higher concentration to an area of lower concentration across plant cellular boundaries, which is advantageously used in both directions by changing the solution chemistry to contain not only compounds which are desired in the product to enhance the flavor, but to remove compounds that taint the product.

Final Stress is a phase of the life cycle roughly corresponding to the first frost of the year where the plant is essentially killed. This plant puts any last stored energy into ensuring offspring survival. Energy stored in tissue in the plant is taken up by buds. Irrigation is ceased and lighting is adjusted appropriately.

Harvest marks the end of the growing phases of the plant and tracking for processing stages is commenced. At this time any residual plant material may be removed from the apparatus. Maintenance, sterilization and replanting of the next crop would occur to repeat the process.

Examples

Figure 2:
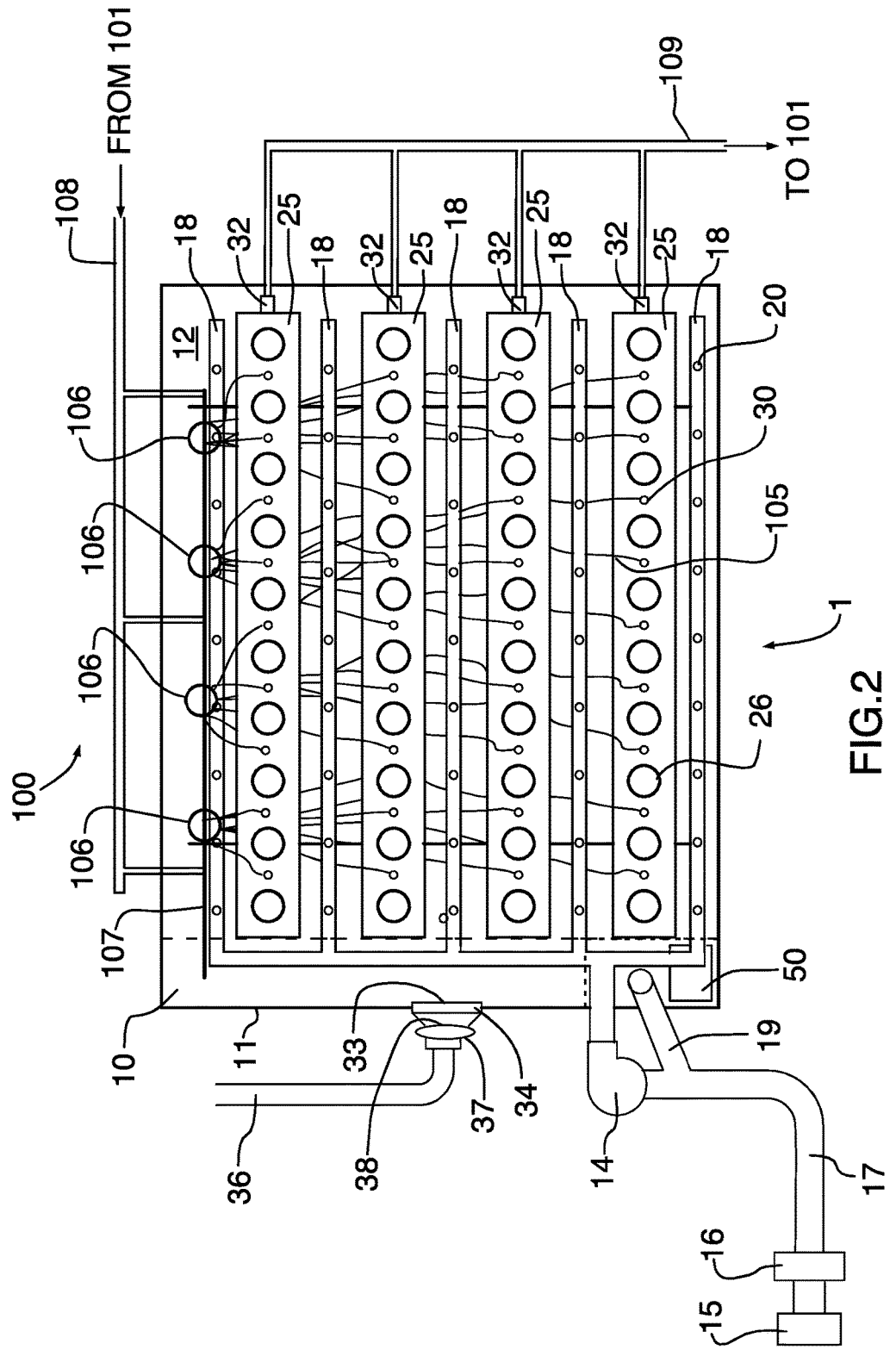
FIG. 2 depicts a schematic plan view of the apparatus for growing marijuana plants comprising a growth chamber.
Figure 3:
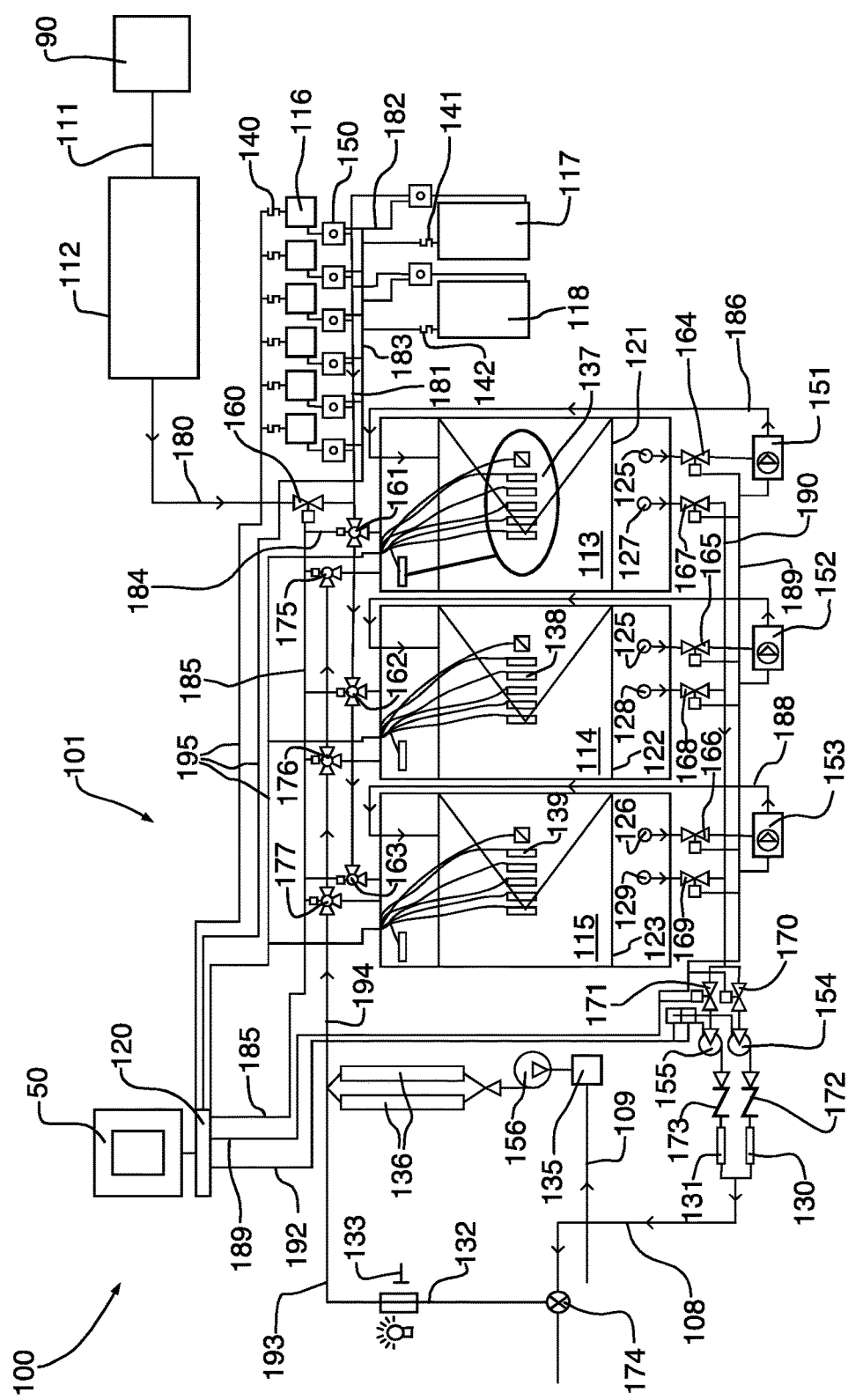
FIG. 3 depicts a schematic diagram of a water treatment zone of a water management system of the apparatus for growing marijuana plants.

Referring to FIG. 1, FIG. 2 and FIG. 3, an embodiment of an apparatus 1 for growing marijuana plants 5 (only one labeled) comprises a growth chamber 10 and a water management system 100 in fluid communication the growth chamber 10. The growth chamber 10 comprises walls 11 bounding an internal space 12 containing a climate controlled micro-climate. Under normal operating conditions, the micro-climate in the internal space 12 is recirculated within the growth chamber 10 by an incoming air fan 14. Air exhaust the growth chamber through an exhaust conduit 36 and make-up air enters through an intake conduit 17. Before entering the growth chamber 10, the incoming air is filtered through a HEPA filter 15, conditioned for temperature and humidity through air conditioner 16 and passed through the intake conduit 17 before being blown by the incoming air fan 14 through an air inlet 23 into a plurality of air blower tubes 18 located in, proximate a bottom of and running a length of the growth chamber 10. The air blower tubes 18 comprise a plurality of blow holes 20 (only one labeled) through which air is vigorously blown to encourage air mixing and circulation within the growth chamber 10.

The growth chamber 10 further comprises a plurality of growing tubes 25 comprising a plurality of apertures 26 (only one labeled) in which the marijuana plants 5 are supported with root balls 27 (only one labeled) contained in an interior 28 of the growing tubes 25 and stems 29 (only one labeled) exterior to the growing tubes 25 but within the growth chamber 10. The growing tubes 25 further comprise a plurality of water inlets 30 (only one labeled) through which water and other chemical components (e.g. nutrients, peroxide, marker dye, flavor additives and the like) may be introduced to the root balls 27 in the interior 28 of the growing tubes 25. Each water inlet 30 is fed by a water feeder conduit 105 forming part of the water management system 100. The water feeder conduits 105 (only one labeled) are in fluid communication with distribution heads 106 in a water header line 107 fluidly connected to a water treatment zone 101 of the water management system 100 through an outgoing feed line 108. Nutrient-rich water sprayed through the water inlets 30 onto the root balls 27 drains through the growing tubes 25 exiting the growing tubes 25 through water outlets 32. From the growing tubes 25, water returns to the water management zone 101 through a return feed line 109 of the water management system 100.

The growth chamber 10 further comprises an air outlet 33 through which the circulating air stream exits the growth chamber 10. An exhaust fan 37 draws outgoing air from the growth chamber 10 through the carbon filter 34 and pushes it out through the exhaust conduit 36. This maintains a slight negative pressure within the growth chamber 10, relative to an external environment outside the growth chamber 10. The carbon filter 34 filters odor-causing compounds before the air is exhausted. An odor sensor 38 proximate and downstream of the carbon filter 34 detects whether any odor-causing compounds are present in the filtered outgoing air in conduit 36. Because the growth chamber 10 is under negative pressure, any leaks in the growth chamber 10 cause air to enter rather than exit the growth chamber. Thus, odor-causing compounds are only able to exit from the growth chamber 10 through the air outlet 33 where the filter 34 and odor sensor 38 is located. An optional filter life sensor 39 is also located at the carbon filter 34 to warn in advance of leakage when the filter needs to be changed.

The growth chamber 10 further comprises lamp fixtures 40 with lamps 41 and lamp ballasts 42 to provide light for growing the marijuana plants 5. A pressure sensor 43, a humidity sensor 44 and a temperature sensor 45 determine the pressure, temperature and relative humidity, respectively, in the growth chamber 10. Other pressure, temperature and humidity sensors may be deployed in the growth chamber 10 at specific locations for determining exact conditions at those locations. An optical imaging sensor 46 (e.g. a camera) provides a view of the interior of the growth chamber 10.

With reference to FIG. 1, FIG. 2 and FIG. 3 and specific reference to FIG. 3, the water management system 100 comprises the water treatment zone 101. There may be one water management system per growth chamber, more than one water management system per growth chamber or more than one growth chamber per water management system. The water treatment zone 101 comprises various tanks, conduits, valves, pumps, sensors and other structures for storing, transporting, diverting and treating water and other chemicals for use in growing the marijuana plants 5. The water management system 100 together with the growth chamber 10 may be automatically controlled by a growing system controller 50 programmed to automatically adjust parameters of the water management system 100 and growth chamber 10 in response to signals sent from the sensors to the growing system controller 50. In this manner, the entire apparatus 1 may be automatically controlled without the need for operator intervention except in the case of emergencies or when adjustments to the program are desired.

Water may be initially supplied to and replenished in the water treatment zone 101 from an external water supply 90, which may be for example city water, well water, and the like. Water from the external water supply 90 may enter into a water deionizer 112 via an external water supply line 111. Deionized water from the water deionizer 112 may be transported through a conduit 180 to one or more mixing and storage tanks (e.g. 113, 114, 115) and one or more chemical supply tubs (e.g. 116, 117, 118). Mixing and storage tanks may include, for example, a water/peroxide tank 113, a first feed cycle tank 114 and a second feed cycle tank 115. Chemical supply tubs may include, for example, one or more nutrient tubs 116 containing nutrients (e.g. sugars, trace elements, fertilizers), alkali, enzymes, flavor additives, marker dyes and the like in concentrated form, an acid tub 117 containing concentrated acid and a hydrogen peroxide tub 118 containing concentrated hydrogen peroxide. A primary deionized water flow valve 160 may control flow of the deionized water from the water deionizer 112 to all of the tanks and tubs.

Chemical components from each of the tubs 116, 117, 118 may be provided in a measured manner through a conduit 181 to one or more of the mixing and storage tanks 113, 114, 115 by metering pumps 150 (only one labeled), each of the tubs 116, 117, 118 having a dedicated metering pump 150. Valves 161, 162, 163 associated respectively with mixing and storage tanks 113, 114, 115 may control whether the water and other chemical components enter the respective tanks depending on current operational requirements. Each of metering pumps 150 may also be in electronic communication with the growing system controller 50 through an electrical conduit 182 (only one labeled), which may be in electronic communication with a master electrical conduit 183 that leads back to a breakout terminal 120 of the growing system controller 50. The breakout terminal 120 may permit distributing control commands from the growing system controller 50 to various sub-systems. Similarly, each of the valves 161, 162, 163 may be in electronic communication with electrical conduits 184 (only one labeled), which may be in electronic communication with a master tank electrical conduit 185 that leads back to the breakout terminal 120. Likewise, the primary deionized water flow valve 160 may be in electronic communication with the master tank electrical conduit 185 that leads back to the breakout terminal 120.

Each mixing and storage tank 113, 114, 115 may comprise a cooling coil 121, 122, 123, respectively, connected to a chiller and pump assembly 151, 152, 153, respectively, for cooling fluid in the tanks 113, 114, 115. The chiller and pump assemblies 151, 152, 153 may further recirculate the fluids in the tanks 113, 114, 115 by receiving fluid from the bottoms of the tanks 113, 114, 115 and pumping the fluid through tank recirculation conduits 186, 187, 188, respectively, back into the tanks 113, 114, 115 proximate the top of the tanks 113, 114, 115. Recirculation permits mixing of the other chemical components in the water and also promotes an even temperature throughout the fluid. The tanks 113, 114, 115 may comprise tank recirculation outlets 124, 125, 126, respectively, in fluid communication with tank recirculation valves 164, 165, 166, respectively, in fluid communication with the chiller and pump assemblies 151, 152, 153, respectively, to permit recirculation of the fluid out from proximate the bottoms of the tanks 113, 114, 115. The tank recirculation valves 164, 165, 166 may be further in electronic communication with tank recirculation electrical conduit 189 that leads back to the breakout terminal 120. The tanks 113, 114, 115 may further comprise tank feed outlets 127, 128, 129, respectively, in fluid communication with a primary tank feed outflow conduit 190 through tank feed valves 167, 168, 169, respectively. The tank feed valves 167, 168, 169 may be further in electronic communication with tank recirculation electrical conduit 189 that leads back to the breakout terminal 120.

Water and other chemical components flowing in the primary tank feed outflow conduit 190 may pass through one or more outgoing feed valves, for example two outgoing feed valves 170, 171, to one or more outgoing feed pumps, for example two outgoing feed pumps 154, 155. The outgoing feed valves 170, 171 may be further in electronic communication with the tank recirculation electrical conduit 189 that leads back to the breakout terminal 120. The outgoing feed pumps 154, 155 may be further in electronic communication with an outgoing feed pump electrical conduit 192 that leads back to the breakout terminal 120. Fluid pumped out of the outgoing feed pumps 154, 155 may pass through one or more check valves, for example two check valves 172, 173, to prevent backwash of fluid into the outgoing feed pumps 154, 155, Fluid from the check valves 172, 173 may pass through one or more particle filters, for example two particle filters 130, 131, before entering the outgoing feed line 108 to be transported to the water header line 107 in the growth chamber 10. Some fluid in outgoing feed line 108 on the way to the growth chamber 10 may be diverted at outgoing feed sampling valve 174 through an outgoing feed sampling conduit 193 into sampling area 132 where a colorimeter 133 (e.g. a spectrophotometer) may be employed to measure levels of various other chemical components (e.g. enzymes, peroxide, or a marker dye as a proxy for other chemical components) in the outgoing fluid feed. The sampled fluid may be recirculated back into the tanks 113, 114, 115 proximate the top of the tanks 113, 114, 115 via a primary tank return conduit 194.

Water and other chemical components returning from the growth chamber 10 to the water treatment zone 101 may arrive in the water treatment zone 101 through the return feed line 109. A return line pump 156 may assist with pumping the fluid away from the growth chamber 10 through the return feed line 109 to screen filter 135. From the screen filter 135, the return line pump 156 may pump the returned fluid through one or more sterilization modules 136 to kill bacteria, mold spores and other pest organisms. Any suitable sterilization module may be employed, for example ultraviolet (UV) sterilizers. Sterilized fluid leaving the sterilization modules 136 may be returned to the tanks 113, 114, 115 via the primary tank return conduit 194. Returning fluid tank valves 175, 176, 177 associated respectively with mixing and storage tanks 113, 114, 115 may control whether the returning water and other chemical components enter the respective tanks depending on current operational requirements. The returning fluid tank valves 175, 176, 177 may be further in electronic communication with the tank recirculation electrical conduit 189 that leads back to the breakout terminal 120.

One or more, preferably all, of the valves and pumps in the water treatment zone 101 may be electrically operable and under the control of the growing system controller 50. While the above description describes the use of electrical conduits for electronic communication, electronic communication may be accomplished in any suitable manner, for example wirelessly, in addition to or instead of through electrical conduits.

Various sensors may be associated with different elements of the water treatment zone 101 to measure various parameters and provide feedback to the growing system controller 50. The growing system controller 50 may be programmed to automatically adjust parameters of the water management system 100 and growth chamber 10 in response to signals sent from the sensors in the water treatment zone 101. Each tank 113, 114, 115 may comprise one or more tank sensors 137, 138, 139 to measure one or more parameters of the fluid in the tanks, for example one or more of temperature, fluid level, oxygen content, pH, total dispersed solids (TDS), concentration of marker dye, concentration of flavor additive, concentration of nutrients, and the like. Each chemical supply tub 116, 117, 118 may also have one or more sensors, for example supply tub sensors 140 (only one labeled), 141 142, respectively, for measuring the amount of chemical remaining the tubs 116, 117, 118. The sensors 137, 138, 139, 140, 141, 142 may be in electronic communication with the growing system controller 50 through sensor electrical lines 195, or in any other suitable manner, for example wirelessly.

Figure 4:
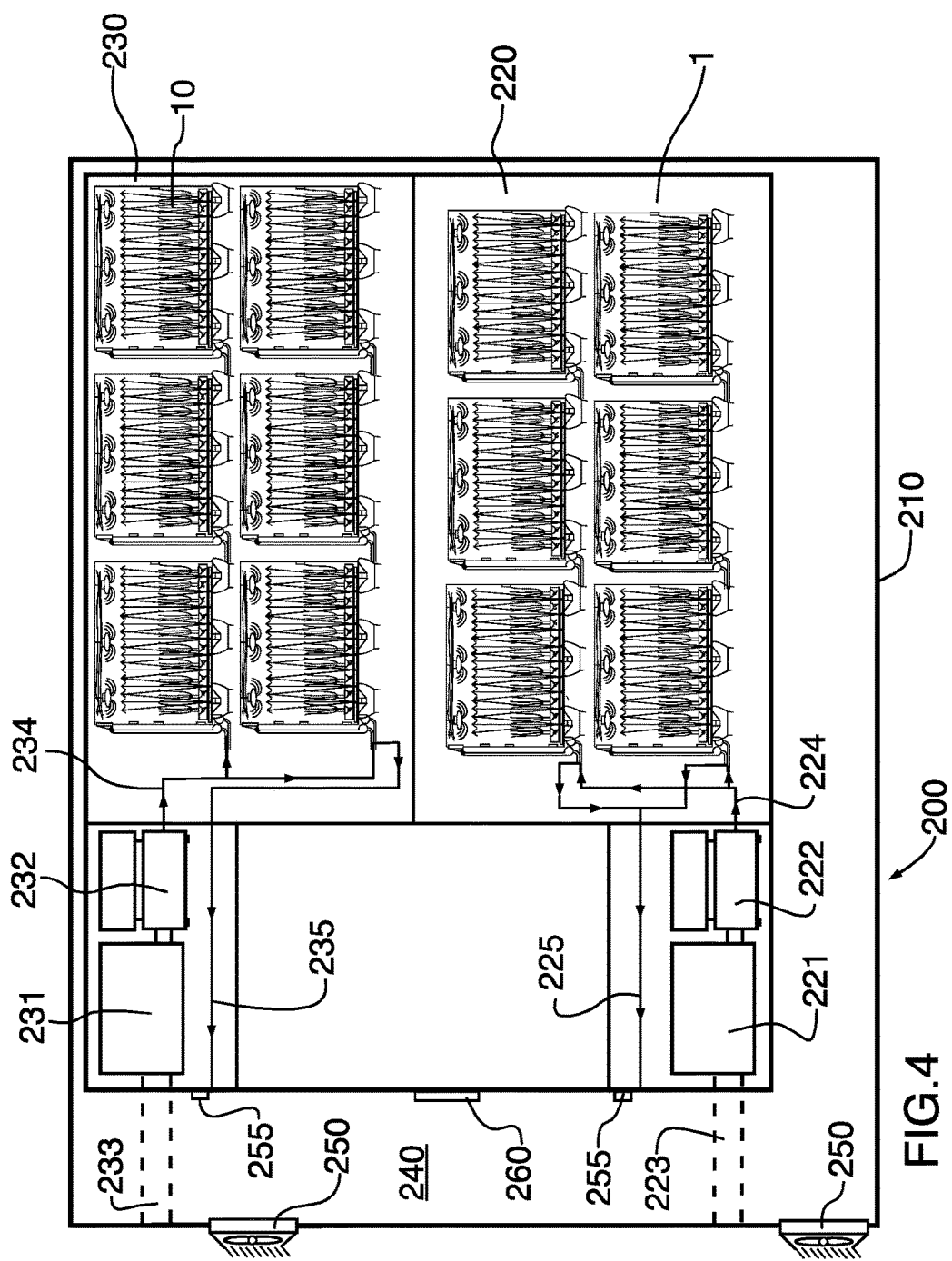
FIG. 4 depicts a schematic diagram of a facility for growing marijuana plants comprising a building having a climate controlled interior space under positive pressure and a plurality of the apparatuses for growing marijuana plants in the interior space.

Referring to FIG. 4, a facility 200 for growing marijuana plants may comprise a building 210 and a plurality of the apparatuses 1 (only one labeled) for growing marijuana plants inside the building 210. In this embodiment, the building comprises two climate controlled areas 220, 230 each comprising six marijuana growing apparatuses 1 for a total of six growth chamber 10 (only one labeled) per area. The two areas 220, 230 separately receive HEPA-filtered and air-conditioned air from separate HEPA air purification systems 221, 231 and air conditioners 222, 232. The HEPA air purification systems 221, 231 receive air through air ducts 223, 233, respectively, from area 240 of the building 210, and the filtered and air conditioned air 224, 234 provide a positive air pressure environment around the apparatuses 1, the interiors of the apparatuses 1 having a relatively lower air pressure than the air pressure in the areas 220, 230. The apparatuses 1 take in the filtered and air conditioned air 224, 234 in areas 220, 230 before venting exhaust air 225, 235 back out of the areas 220, 230 through ducts into the area 240. Building fans 250 vent exhausted air 225, 235 to an exterior of the building 210 and building odor sensors 255 detect any odors being carried by the exhausted air 225, 235. A controller 260 in the building may be in electronic communication with the air conditioners 222, 232, building odor sensors 255 and/or the building fans 250 so that if one or more of the building odor sensors 255 detect odors the exhausted air 225, 235, the controller 260 can do one or more of reduce fan speed of the air conditioners 222, 232 and reverse fan direction of the building fans 250 to provide a negative pressure in the areas 220, 230 relative to the air pressure in the area 240. In this manner, air from an exterior of the building 210 will flow into the building to reduce the chance of odors leaking from the building while remedial action is taken. Further, the controller 260 may be in electronic communication with the controllers of the apparatuses 1 to cease operations of the growth chambers in the event of an odor being detected by the building odor sensors 255.

Figure 5:
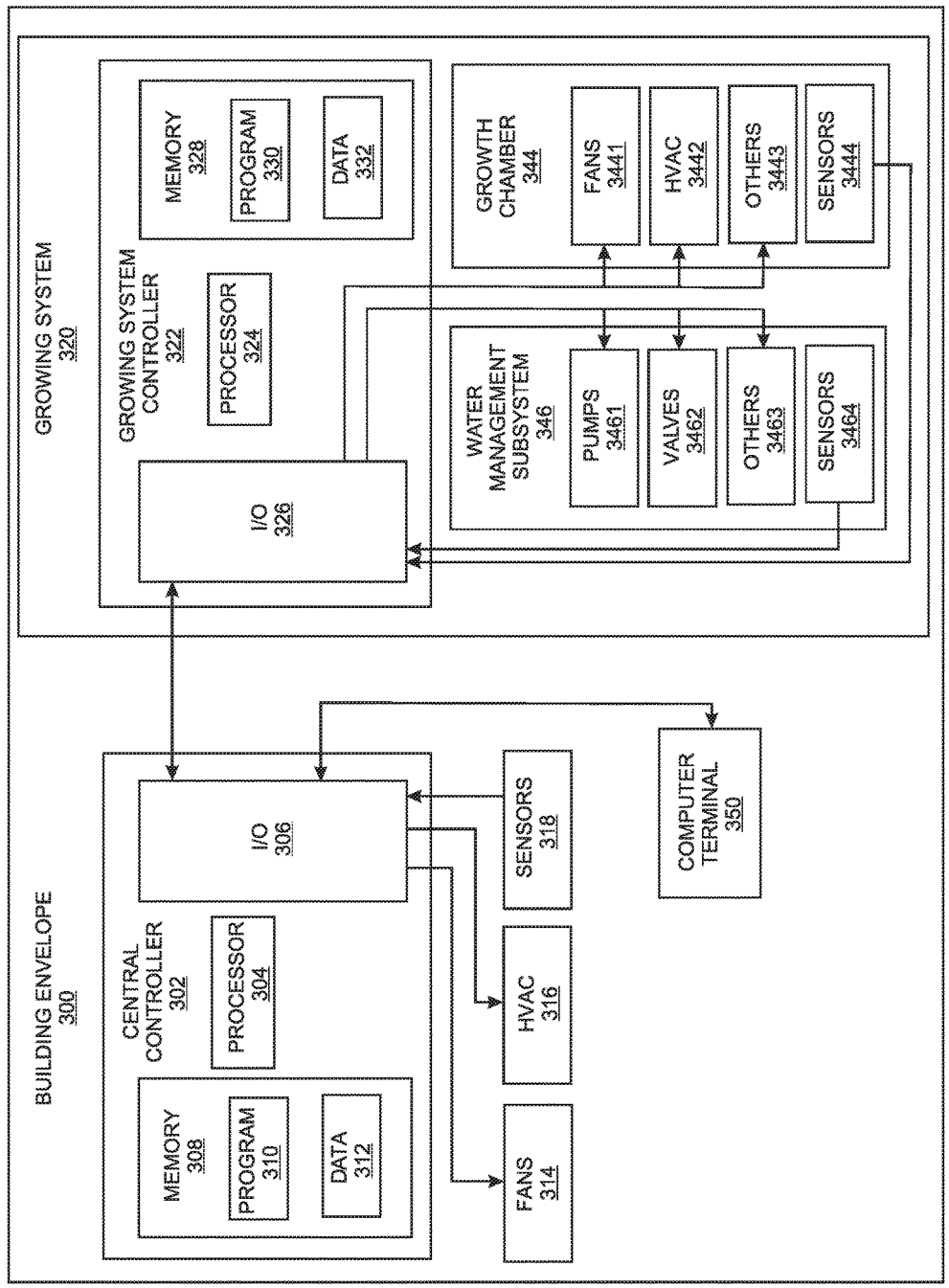
FIG. 5 depicts a schematic diagram showing feedback control for a facility for growing marijuana plants.

Referring to FIG. 5, a feedback control system for a facility for growing marijuana plants is shown. The facility 375 comprises a growing system 320 situated in an interior space of a building envelope 300. The growing system 320 comprises a growth chamber 344, a water management system 346 and a growing system controller 322 in electronic communication with elements of the growth chamber 344 and water management system 346. The growing system controller 322 comprises a memory 328 to store data 332, for example operational parameters from the growth chamber 344 and water management system 346, and computer executable code in the form of programs 330 for operating the growing system 320. A processor 324 executes the programs 330 utilizing the data 332 and sends signals through an input/output (I/O) device 326 to pumps 3461, valves 3462, other water management devices 3464 (e.g. UV sterilizers) of the water management system 346 and to fans 3441, HVAC units 3442 and other growth chamber devices 3443 (e.g. lamps) of the growth chamber 344 to operate the growing system 320. Sensors 3444 associated with the growth chamber 344 and sensors 3464 in association with the water management system 346 provide signals to the growing system controller 322 through the I/O device 326, the signals providing an indication of the status of various operational parameters. The signals are interpreted by the processor 324 and stored as data 332 in the memory 328. The programs 330 may automatically utilize the data to determine whether to make changes to the operational status of the elements of the growth chamber 344 and/or water management system 346.

The building envelope 300 comprises a central controller 302 in electronic communication with elements of the building envelope 300. The central controller 302 comprises a memory 308 to store data 312, for example operational parameters of fans 314 and HVAC systems 316, and computer executable code in the form of programs 310 for operating the facility 375. A processor 304 executes the programs 331 utilizing the data 312 and sends signals through an input/output (I/O) device 306 to the fans 314, the HVAC systems 316 and/or the growing system 320. Sensors 318 associated with the building envelope 300 provide signals to the central controller 302 through the I/O device 306, the signals providing an indication of the status of various operational parameters of the building envelope 300.

Further, the growing system controller 322 sends signals to the central controller 302, the signals providing an indication of the status of various operational parameters of the growing system 320. The signals are interpreted by the processor 304 and stored as data 312 in the memory 308. The programs 310 may automatically utilize the data to determine whether to make changes to the operational status of the building envelope 300 and/or the growing system 320.

Thus, feedback signals received from the sensors 318 of the building envelope 300 and the sensors 3444, 3464 of the growing system 320 may be processed together by the central controller 302 to determine whether any changes to the facility 375 need to be made and then to implement the changes by sending instructions to elements of the building envelope 300, growing system 320 or both. Such an integrated feedback approach permits optimization of growing conditions and prevention of odor release and crop contamination without necessarily requiring operating intervention. However, the central controller 302 may also be in electronic communication with a user interface, for example a computer terminal 350 where an operator may monitor the status of the facility, receive automated alerts and/or alarms from the central controller 302 and/or manually input changes to the programs 310, 330 and/or data 312, 332.

The novel features will become apparent to those of skill in the art upon examination of the description. It should be understood, however, that the scope of the claims should not be limited by the embodiments, but should be given the broadest interpretation consistent with the wording of the claims and the specification as a whole.

The invention claimed is:

1. An apparatus for growing marijuana plants comprising:
   a growth chamber containing a climate controlled microclimate under negative air pressure;
   at least one marijuana plant support structure situated in the growth chamber for supporting a marijuana plant whereby roots of the marijuana plant are exposed to air in the growth chamber;
   a water management system in fluid communication with the plant support structure for delivering water and other chemical components besides water to at least the roots of the marijuana plant;
   at least one sensor for sensing at least one parameter of the growth chamber, water management system or marijuana plant, the at least one sensor comprising an optical device for detecting size and/or color of at least a portion of the marijuana plant, a sensor for sensing peroxide level in the water, a sensor for sensing nutrient level in the water, a sensor for sensing flavor additive level in the water and a sensor for sensing a marker dye level in the water; and,
   a controller in electronic communication with the at least one sensor and one or more of the growth chamber and water management system, the controller for controlling the growth chamber, water management system or both in response to a signal from the at least one sensor.

2. The apparatus according to claim 1, wherein the at least one sensor comprises a spectrophotometer.

3. The apparatus according to claim 1, wherein the water management system comprises a water treatment zone, conduits, one or more pumps, one or more valves and one or more storage tanks for recirculating the water and the other chemical components between the plant support structure and the water treatment zone and for transferring, storing and/or mixing the water and the other chemical components, and wherein the at least one parameter comprises a parameter of the recirculating water and other chemical components, the at least one sensor comprising a sensor for sensing the parameter of the recirculating water and other chemical components.

4. The apparatus according to claim 1, further comprising one or more lamps for providing light to the plants in the growth chamber.

5. The apparatus according to claim 1, wherein the plant support structure comprises a tube with apertures in which the marijuana plant is supported so that the roots are within the tube and a stem is outside the tube when the plant is supported in the tube.

6. An apparatus for growing marijuana plants comprising:
a growth chamber containing a climate controlled micro climate under negative air pressure;
at least one marijuana plant support structure situated in the growth chamber, the plant support structure configured to support a marijuana plant whereby roots of the marijuana plant are exposed to air in the growth chamber;
a water management system in fluid communication with the plant support structure for delivering water and other chemical components besides water to at least the roots of the marijuana plant;
at least one sensor for sensing at least one parameter of the growth chamber, water management system or marijuana plant, the at least one sensor comprising an optical device for detecting size and/or color of at least a portion of the marijuana plant, wherein the at least one sensor further comprises a colorimeter for measuring levels of one or more of the other chemical components in the water management system; and
a controller in electronic communication with the at least one sensor and one or more of the growth chamber and water management system, the controller for controlling the growth chamber water management system or both in response to a signal from the at least one sensor.

7. The apparatus according to claim 6, wherein the one or more of the other chemical components comprises a marker dye and the colorimeter comprises a spectrophotometer for measuring levels of the marker dye in the water management system.

* * * * *